US00PP08308P

United States Patent [19]

King-Turner et al.

[11] Patent Number: Plant 8,308

[45] Date of Patent: Jul. 20, 1993

[54] PEAR TREE NAMED *'TAYLOR'S GOLD'*

[76] Inventors: Michael B. King-Turner; Wendy M. King-Turner, both of Umukuri Road, RD 3, Motueka, New Zealand

[21] Appl. No.: 761,192

[22] Filed: Sep. 16, 1991

[51] Int. Cl.[5] ..... A01H 5/00

[52] U.S. Cl. ..... Plt./36

[58] Field of Search ..... Plt. 36

*Primary Examiner*—James R. Feyrer

*Assistant Examiner*—E. F. McElwain

*Attorney, Agent, or Firm*—Quarles & Brady

[57] ABSTRACT

A new and distinctive variety of pear is described. The variety is a mutation of the 'Doyenne du Comice' variety. The variety is distinguished by its fully russeted skin which makes it easier to handle than the 'Doyenne du Comice'. The new variety has been named 'Taylor's Gold'.

2 Drawing Sheets

SUMMARY OF THE INVENTION

The present invention relates to a new and distinct pear variety. More particularly the new cultivar is designated 'Taylor's Gold' and is a mutation of the 'Doyenne du Comice' variety.

The variety was discovered on the inventors' property at Motueka, New Zealand. After the variety was discovered, it was asexually reproduced by grafting onto root stock of the Pyrus calleryana and Cydonia oblonga PQ BA 29 varieties on the same property. The fruit was first observed on the reproduced plants in 1989.

Asexual propagation shows that the unique combination of characteristics come true to form and are established and transmitted through succeeding propagations.

BRIEF DESCRIPTION OF THE DRAWINGS

The invention may be more fully understood by having reference to the accompanying photographic color reproductions.

View A is a top view of a pear of the 'Taylor'Gold' variety,

View B is a side view of a pear of the 'Taylor's Gold' variety,

View C is a bottom view of a pear of the 'Taylor's Gold' variety,

View D is a bottom view of a pear of the 'Doyenne du Comice' variety,

View E is a side view of a pear of the 'Doyenne du Comice' variety,

View F is a top view of a pear of the 'Doyenne du Comice' variety.

Figure 1:
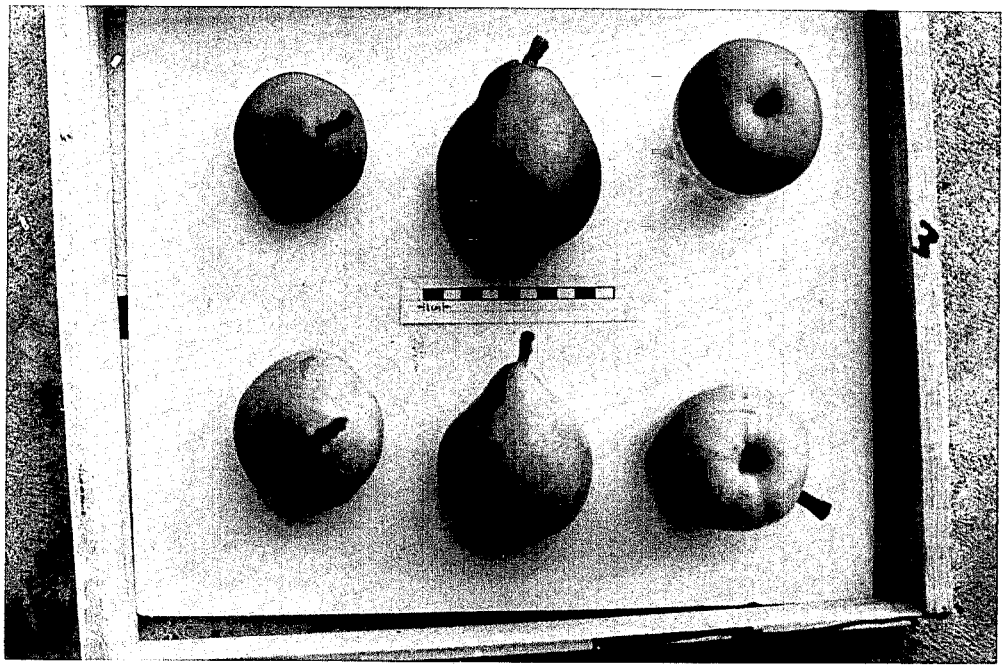
FIG. 1: shows 'Taylor's Gold' (top) in comparison with 'Doyenne du Comice' (bottom). Beginning in the upper right corner and proceeding clockwise.
Figure 2:
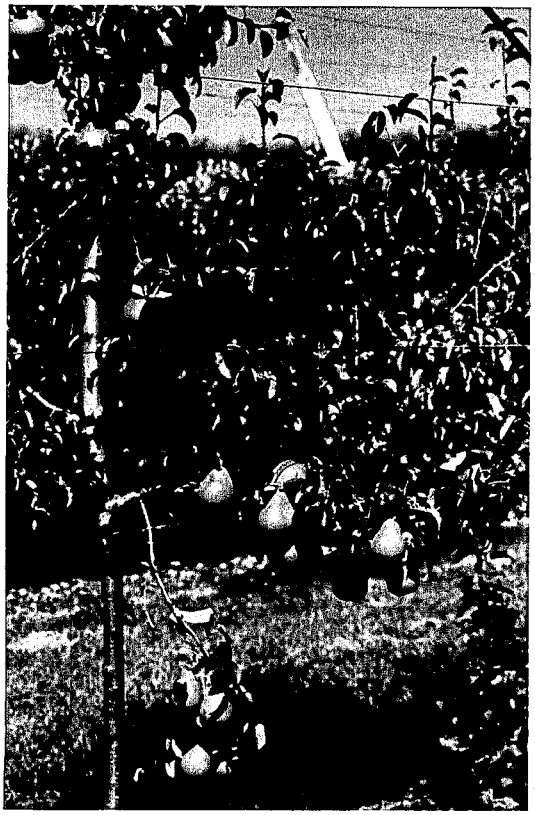

FIG. 2: shows a tree of 'Taylor's Gold' with fruit.

DETAILED DESCRIPTION

The following is a detailed description of the new variety with color terminology in accordance with the Munsell Colour System except where general color terms of ordinary dictionary significance are obvious. The color measurements for the fruit were taken after the fruit had been stored for fourteen weeks.

The distinctive characteristics of this new pear cultivar described in detail below were observed in 1990/91 season. The specimens described were grown at Motueka, New Zealand. The comparisons were with 'Doyenne du Comice'.

'Taylor's Gold' is distinct from 'Doyenne du Comice' as illustrated in that 'Taylor's Gold' is fully russeted breaks leaf dormancy 7 to 10 days earlier, and the fruit is smaller. In other respects 'Taylor's Gold' is similar to 'Doyenne du Comice'.

BOTANICAL DESCRIPTION

PLANT

On a one year old tree the plant demonstrates medium vigour as per 'Doyenne du Comice'. Growth observed on a one year old tree is straight to slightly wavy and there are few side shoots. Tree habit is as per 'Doyenne du Comice'.

While the amount of growth in any one season depends upon such factors as root stock, soil type, irrigation and crop load, both 'Taylor's Gold' and 'Doyenne du Comice' express the same growth habits when grown under similar conditions. The growth habit of both plants is approximately 800 mm of growth averaged and distributed over the whole tree.

There are a medium number of lenticels on the one year old vegetative shoots and the shape of the vegetative buds is medium, i.e., inbetween squat and elongated. The position of the vegetative buds relative to the shoots is free. The color of the first and second year wood is brown 7.5YR 4/2, and the third year wood is brown 7.5YR 4/1.

The shape of the fruit bud is pointed. In the young shoot the color of the extremity on rapidly growing material is reddish green and the pubescene of the tip is as for 'Doyenne du Comice'.

The attitude of the leaf blade in relation to the shoot is horizontal and the leaf blade length is medium (approximately 75 mm). The leaf blade is approximately 50 mm. The length to breadth ratio of the leaf blade is 1.5 and the general shape in cross-section of the leaf blade is inbetween flat and up-cupped. The shape of the base is obtuse to flat and the shape of the leaf blade tip is broad acuminate. The leaf blade indentation of margin is crenate with slight tendency to serrate. The depth of indentation of margin is shallow and there is little curvature of the midrib. Very few or no glands are present on the midrib.

The angle of the petiole to the shoot is 30 to 60 degrees and the petiole length of 'Taylor's Gold' is approximately 35 mm. The petiole length of 'Doyenne du Comice' is approximately 43 mm.

The stipule is only present on strong growing annual shoots and is absent on spur leaves. The distance of the stipule from the base of the petiole is medium.

Leaf emergence on 'Taylor's Gold' is 7 to 10 days earlier than 'Doyenne du Comice.' The leaf emergence dates for the 1989 and 1990 seasons were between 17 and 19 September for 'Taylor's Gold' and between 25 and 27 September for 'Doyenne du Comice'.

FLOWERS AND FLOWERING

There are many flowers on the inflorescences as per 'Doyenne du Comice'. Actual flowering time for the 1989 and 1990 seasons was from 27 September to 14 October for 'Taylor's Gold'. Blossom follows leaf emergence as the dates above indicate. The average full bloom date for the last two years was 5 October, the same as 'Doyenne du Comice'. The petals are separate and do not overlap. The length of the pedicel and sepal is as per 'Doyenne du Comice' as is the position of the sepal, i.e., curved towards the pedicel. The length of the petal is as 'Doyenne du Comice'. The length/breadth ratio of the petal is longer than broad. The shape of the petal base is flat tending to U shaped. The undulation of petal margins is medium and the length of the petal claw is medium tending to short. The stigma is just below the anther. The anther size is medium. The shape of the receptacle is slightly hollowed. The petal color is white 2.5Y 9/12.

FRUIT AND FRUITING

The size of 'Taylor's Gold' is slightly smaller than 'Doyenne du Comice'. 'Doyenne du Comice' is large whereas 'Taylor's Gold' tends to medium to large in size. While fruit weight varies with the influence of factors such as climate, the average fruit weight for 'Taylor's Gold' and 'Doyenne du Comice' grown under the same conditions were 275 g and 312 g, respectively. The fruit shape in profile is straight tending to convex as for 'Doyenne du Comice'. The position of maximum diameter is towards the base. The fruit length relative to the maximum diameter is intermediate. Russet covers the entire surface of the fruit. The color of the skin is brown 7.5YR 6/6. A red blush is observed on some fruit in some seasons. In comparison the skin color of 'Doyenne du Comice' ranges from green-yellow 5BG 4/8 to yellow 5Y 7/10. Lenticels on the fruit are numerous but cannot be color coded. The length and thickness of the stalk is for 'Doyenne du Comice', short and thin and the shape of the stalk is straight. The insertion of the stalk is oblique and the cavity of the stalk is as per 'Doyenne du Comice'. The size of the eye is as for 'Doyenne du Comice' and the opening of the eye at harvest is inbetween open and closed. The pose of the sepals at harvest is upright and the length of the sepals is short. The diameter of the core and shape of cells of the core is as per 'Doyenne du Comice'. The seeds are a tear drop shape and of a color brown/black 10RP 2/2. The texture of the flesh is fine, melting. The taste is sweet and the juiciness is strong as for 'Doyenne du Comice'. The color of the flesh is white/cream 10YR 8/1. The picking time appears to be the same as 'Doyenne du Comice' which was 5 to 8 March through to 26 to 29 March in 1990.

Both 'Taylor's Gold' and 'Doyenne du Comice' appear to respond similarly to disease in that they have a higher resistance than most other pear varieties to most diseases with the exception of *Pseudomonas syringae* to which both 'Taylor's Gold' and 'Doyenne du Comice' are susceptible.

We claim:

1. A new and distinct variety of pear tree which is a mutation of the 'Doyenne du Comice' variety, substantially as herein shown and described and identified by the characteristics enumerated above.

* * * * *